(12) United States Patent
Ke et al.

(10) Patent No.: US 9,657,084 B2
(45) Date of Patent: May 23, 2017

(54) FUSION PROTEIN INHIBITING ANGIOGENESIS OR GROWTH AND USE THEREOF

(71) Applicant: CHENGDU KANGHONG BIOTECHNOLOGIES CO., LTD., ChengDu, Sichuan (CN)

(72) Inventors: Xiao Ke, Sichuan (CN); Xiaoping Gao, Sichuan (CN)

(73) Assignee: Chengdu Kanghong Biotechnologies Co., LTD. (CN)

( * ) Notice: Subject to any disclaimer, the term of this patent is extended or adjusted under 35 U.S.C. 154(b) by 0 days.

(21) Appl. No.: 15/109,422

(22) PCT Filed: Jan. 23, 2015

(86) PCT No.: PCT/CN2015/071434
§ 371 (c)(1),
(2) Date: Jun. 30, 2016

(87) PCT Pub. No.: WO2015/110067
PCT Pub. Date: Jul. 30, 2015

(65) Prior Publication Data
US 2017/0002056 A1    Jan. 5, 2017

(30) Foreign Application Priority Data
Jan. 25, 2014 (CN) .......................... 2014 1 0035738

(51) Int. Cl.
| A61K 38/00 | (2006.01) |
| C07K 14/71 | (2006.01) |
| C07K 19/00 | (2006.01) |
| C12N 5/10 | (2006.01) |
| C12N 5/16 | (2006.01) |
| C12N 15/12 | (2006.01) |

(52) U.S. Cl.
CPC .............. *C07K 14/71* (2013.01); *A61K 38/00* (2013.01); *C07K 2319/30* (2013.01); *C07K 2319/35* (2013.01)

(58) Field of Classification Search
None
See application file for complete search history.

(56) References Cited

U.S. PATENT DOCUMENTS

| 7,750,138 | B2 * | 7/2010 | Fang ................. C07K 14/4703 435/320.1 |
| 8,216,575 | B2 * | 7/2012 | Yu ......................... C07K 14/71 424/134.1 |
| 2008/0206238 | A1 | 8/2008 | Liu |
| 2010/0272719 | A1 | 10/2010 | Yu |

FOREIGN PATENT DOCUMENTS

| CN | 1793179 A | 6/2006 |
| CN | 101279092 A | 8/2008 |
| JP | 2008-502738 | 1/2008 |
| RU | 2011141522 A | 4/2013 |

OTHER PUBLICATIONS

International Search Report for PCT/CN2015/071434, Apr. 13, 2015.
Database USPTO Proteins [Online], "Sequence 8 from U.S. Pat. No. 8,216,575," XP002766419, dated Jul. 23, 2012 (1 page).

* cited by examiner

*Primary Examiner* — Marianne P Allen
(74) *Attorney, Agent, or Firm* — Brinks Gilson & Lione; Ryan L. Marshall; Jonathan Hartley

(57) ABSTRACT

Provided are a fusion protein inhibiting angiogenesis or vascular growth, coding sequence thereof, vector comprising the coding sequence, host cell, pharmaceutical composition and use of the fusion protein. The fusion protein of the present invention has high thermostability, and has a dramatic decline in the protein aggregation formation rate in a fermentation process, and a significant increase in the purity and yield of the protein, and has better biological activity.

12 Claims, 2 Drawing Sheets

FUSION PROTEIN INHIBITING ANGIOGENESIS OR GROWTH AND USE THEREOF

REFERENCE TO EARLIER FILED APPLICATIONS

This application claims the benefit of the filing date of PCT Application No. PCT/CN2015/071434 filed 23 Jan. 2015 which claims priority to Chinese Patent Application No. 201410035738.1 filed 25 Jan. 2014, the disclosures of which are hereby incorporated by reference in their entirety.

FIELD OF THE INVENTION

The present invention relates to the field of genetic engineering. Particularly, the present application relates to a fusion protein inhibiting angiogenesis or vascular growth.

BACKGROUND OF THE INVENTION

Under normal physiological condition, angiogenesis is a process tightly regulated by several factors and it plays a vital part in repairing and maintaining the normal function of the body. However, rapid growth of blood vessels inside tumor is a common clinical phenomenon. It is demonstrated in many animal models and clinical studies that the inhibition of angiogenesis in tumor can inhibit the growth of tumor and induce the death of tumor cell, so that therapeutic effect is achieved. Therefore, the inhibition of angiogenesis has become an important trend for the development of anti-tumor drugs. Macromolecule anti-angiogenesis drugs, such as Avastin, have been approved by the FDA. There are also drugs under pre-clinical and clinical studies. In addition, new anti-angiogenesis drugs are also widely used in the treatment of angiogenesis-related diseases such as age-related macular degeneration (AMD), diabetic retinopathy, and result in significant therapeutic effect.

Angiogenesis is a complex process regulated by many active biological factors. A key process in angiogenesis is the binding and the activation of endothelial cell surface receptor by various growth factors, which control the activity of endothelial cell via intracellular tyrosine phosphorylation signalling and improve angiogenesis. Among these growth factors, vascular endothelial cell growth factor (VEGF) is the most important factor involved in the control of angiogenesis. VEGF is the most potent and the most specific factor in the induction and improvement of angiogenesis. It is overexpressed in almost all human tumors and thus has become an important molecular target in the development of anti-tumor therapy. VEGF has many receptors on the surface of vascular endothelial cell, including VEGFR-1 (also named as Flt-1) and VEGFR-2 (also named as KDR or Flk-1). VEGFR-1 and VEGFR-2 both comprise an extracelluar portion, composed of 7 immunoglobulin-like domains (D1-D7) capable of binding VEGF, and an intracellular portion comprising tyrosine kinase group. Once the receptor is activated by VEGF, the intracellular tyrosine kinase gene is phosphorylated, which results in a signaling cascade and eventually leads to angiogenesis. Due to the importance of VEGF signaling to angiogenesis, blocking VEGF or VEGF receptor to inhibit angiogenesis has significant anticancer effect and is also important for the treatment of other angiogenesis-related diseases such as retinal vasculopathy.

The stability of fusion protein agents has an important influence on their biotechnical applications, and is also vital for the improvement of drug quality and realization of industrial production. The spacial structure of a protein changes under certain physical and chemical conditions, which in turn leads to the change in physical and chemical properties and loss of biological activity. This is called protein denaturation, which is used to describe the process that a protein changes its intramolecular structure and properties when subjected to the influence of physical or chemical factors. Detection of thermal stability of a protein can be used to determine the denaturation effectively and thus is used as a stability test for protein during the development of therapeutic proteins. The detection of thermal stability is mainly carried out by irradiating a protein sample with UV light so that the protein sample emits fluorescence, and determining the denaturation temperature (Tm) of the protein sample by measuring the wavelength and the light intensity of emitted fluorescence, which reflect the change in its structure. Also, protein aggregation is detected by UV excitation using static light scattering. The light intensity of a protein sample changes significantly between aggregation and non-aggregation states. The aggregation onset temperature (Tagg) of a protein sample can be detected accurately according to the change in light intensity. The stability of a protein is reflected by denaturation temperature (Tm) and aggregation onset temperature (Tagg) of the protein.

The constraint conditions for development of macromolecular drugs include the therapeutic effect, the stability, and the feasibility of industrial production of the therapeutic agent. It is necessary to find a drug inhibiting angiogenesis or vascular growth with determined therapeutic effect and high stability.

DESCRIPTION OF THE INVENTION

An object of the present invention is to provide a fusion protein for the inhibition of angiogenesis or vascular growth with determined therapeutic effect and high stability, wherein the fusion protein inhibits angiogenesis or vascular growth by blocking VEGF signaling.

To achieve the above object, the following technical solutions are provided.

In one aspect, the present invention provides a fusion protein for the inhibition of angiogenesis and vascular growth, composed of a human VEGF receptor fragment and an Fc fragment of human immunoglobulin linked thereto, wherein the amino acid sequence of the VEGF receptor fragment is as shown in SEQ ID NO: 1, SEQ ID NO: 3 or SEQ ID NO: 5.

In one embodiment, the Fc fragment of human immunoglobulin of the fusion protein is selected from the group consisting of the following sequences: IgG1 Fc (the amino acid sequence of which is SEQ ID NO: 7), IgG2 Fc (the amino acid sequence of which is SEQ ID NO: 8), IgG3 Fc (the amino acid sequence of which is SEQ ID NO: 9), and IgG4 Fc (the amino acid sequence of which is SEQ ID NO: 10).

In a further embodiment, the fusion protein is,

KH02, the amino acid sequence of which is as shown in SEQ ID NO: 14;

KH03, the amino acid sequence of which is as shown in SEQ ID NO: 16; or

KH04, the amino acid sequence of which is as shown in SEQ ID NO: 18.

In another aspect, the present invention provides a nucleotide sequence encoding the fusion protein. Preferably, the nucleotide sequence is, kh02 encoding fusion protein KH02, the nucleotide sequence of which is as shown in SEQ ID NO: 13;

kh03 encoding fusion protein KH03, the nucleotide sequence of which is as shown in SEQ ID NO: 15; or kh04 encoding fusion protein KH04, the nucleotide sequence of which is as shown in SEQ ID NO: 17.

In another aspect, the present invention provides an expression vector or a host cell expressing the fusion protein, wherein the expression vector comprises the above nucleotide sequence of the fusion protein. The expression vector can be a recombinant eukaryotic expression vector, preferably mammalian cell expression vector. The expression vector can also be a recombinant viral expression vector, preferably adeno-associated virus or adenovirus vector. The expression vector is capable of replication and expression in the transformed host cell. Preferably, the host cell is CHO cell or its subline, or 293 cell or its subline.

In another aspect, the present invention provides a method for preparing the fusion protein, comprising introducing the above expression vector into a suitable host cell and expressing the fusion protein.

In another aspect, the present invention provides a pharmaceutical composition comprising the fusion protein of the present invention and pharmaceutically acceptable carrier or excipient, which is conventionally used in the art. Preferably, the dosage form of the formulation of the pharmaceutical composition is injection, freeze-dried injection powder or ophthalmic gel. The formulation can be prepared by methods known in the art.

In another aspect, the present invention provides use of the above fusion protein in the preparation of a medicament for treating diseases caused by angiogenesis or vascular growth, wherein the diseases caused by angiogenesis or vascular growth are preferably tumor or diseases caused by angiogenesis in eye, where the diseases caused by angiogenesis in eye are preferably age-related macular degeneration, diabetic retinopathy, chorioretinopathy, etc.

In another aspect, the present invention provides a method for treating diseases caused by angiogenesis or vascular growth comprising administrating the fusion protein or pharmaceutical composition of the present invention to a patient in need thereof, wherein the diseases caused by angiogenesis or vascular growth are preferably tumor or diseases caused by angiogenesis in eye, where the diseases caused by angiogenesis in eye are preferably age-related macular degeneration, diabetic retinopathy, chorioretinopathy, etc.

The fusion protein of the present invention has high thermal stability, and thereby the formation of protein aggregates during fermentation is significantly reduced and the purity and yield of the protein is significantly improved. Also, the present fusion protein has good biological activities.

EXAMPLES

Figure 1:
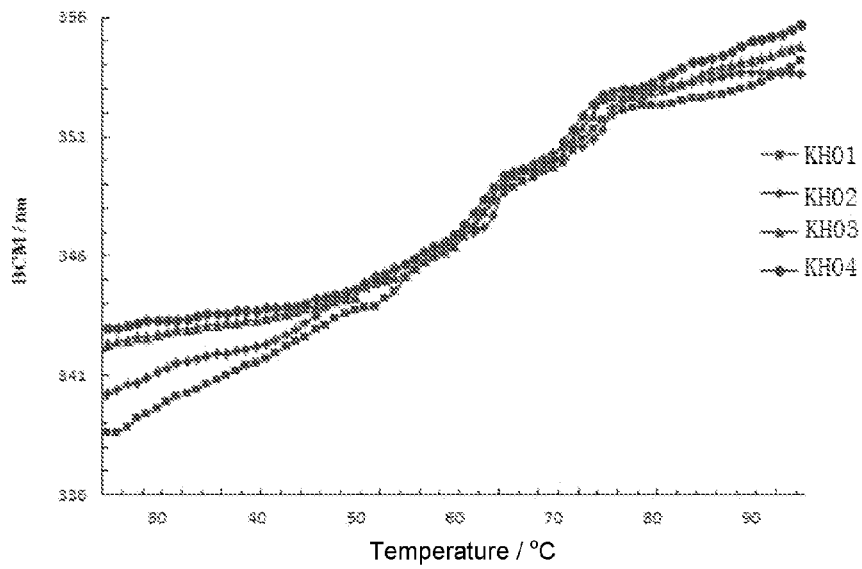
FIG. 1 is a graph showing the tendency for thermal denaturation of the VEGF receptor fusion protein. The curve in the graph reflects the increase of internal fluorescence peak of the protein along with the rise of the temperature. The ordinate BCM (nm) shows internal fluorescence peak, while the abscissa shows the temperature.

The present invention will be further described through the following Examples. It is to be understood that these Examples are only included to illustrate the present invention and the present invention is not limited to these Examples. Any modification a person skilled in the art could make in light of the present disclosure falls into the scope covered by the claims.

Description of the Sequences

Fragment 1 of human VEGF receptor: the amino acid sequence is SEQ ID NO: 1, the nucleotide sequence is SEQ ID NO: 2;

Fragment 2 of human VEGF receptor: the amino acid sequence is SEQ ID NO: 3, the nucleotide sequence is SEQ ID NO: 4;

Fragment 3 of human VEGF receptor: the amino acid sequence is SEQ ID NO: 5, the nucleotide sequence is SEQ ID NO: 6;

Fusion protein KH01: the amino acid sequence is SEQ ID NO: 12, the nucleotide sequence is SEQ ID NO: 11;

Fusion protein KH02: the amino acid sequence is SEQ ID NO: 14, the nucleotide sequence is SEQ ID NO: 13;

Fusion protein KH03: the amino acid sequence is SEQ ID NO: 16, the nucleotide sequence is SEQ ID NO: 15;

Fusion protein KH04: the amino acid sequence is SEQ ID NO: 18, the nucleotide sequence is SEQ ID NO: 17;

Fusion protein KH05: the amino acid sequence is SEQ ID NO: 20, the nucleotide sequence is SEQ ID NO: 19.

Example 1: Preparation of Fusion Proteins

Material or Reagents

PCR kit (comprising 5×buffer, dNTP and Phusion enzyme): M0530L, NEB Corp.

Agarose gel electrophoresis: IQ300, GE Corp.

Buffer 4 (lot no.: 0101201):NEB Corp.

Avrll: R0174L, NEB Corp.

BstZ17I: R0594L, NEB Corp.

PCR product purification kit: QIAGEN Corp., CAT: 28106

10×T4 buffer: B0202S, NEB Corp.

T4 DNA ligase: M0202L, NEB Corp.

Top10 *E. coli*: CB104, TIANGEN Corp.

2YT(KAN) plate culture medium: Shanghai Rui Cong Laboratory Equipment Co., Ltd.

Freedom™ CHO-S™ Kit: A13696-01, LIFE TECHNOLOGIES CORPORATION.

Clone Pix FL: Genetix Corp.

HiTrap protein A agarose affinity chromatography column: HiTrap protein A HP, 5×1 ml; GE Corp.

PBS buffer (20 mM phosphate, pH 7.4): SD117-500 ml, Shanghai Biotech Co., Ltd.

ForteBio bio-molecular interaction detector: Octet QKe, Pall Corp.

Analyzer for thermal stability of protein: Optim2, Avacta Corp.

VEGF: R&D Systems Inc.

NHS-LCLC-Biotin: Thermo Corp.

1. Construction of Plasmid Comprising Sequences Encoding Fusion Protein.

1.1 Synthesis of Genes and Primers

Synthetic fragments 1 (SEQ ID NO: 21) and 2 (SEQ ID NO: 22) and primers P1-P10 (sequences are shown in SEQ ID NO: 23-32) were synthesized by Beijing GENEWIZ, Inc. Synthetic fragments 1 and 2 were recombined into plasmid vector pUC19 (Beijing GENEWIZ, Inc.). Synthetic fragment 1 comprises nucleotide sequence encoding human VEGF receptor fragment and signal peptide sequence, synthetic fragment 2 comprises coding sequence for human IgG1 Fc. The coding sequences for the present fusion proteins were constructed by PCR using the below primers and synthetic fragments 1 and 2 as the template for constructing respective fusion proteins.

1.2 Obtaining the Coding Sequences for Fusion Proteins.

Coding sequence for each fusion protein was amplified in two parts, wherein the first part is human VEGF receptor fragment; and the second part is human IgG1 Fc fragment. The respective target fragment for each part was obtained by the specific primers, and then the human VEGF receptor fragment and human IgG1 Fc fragment were linked by overlapping PCR, giving the final full gene sequence. The reaction system for the amplification PCR of both the first and the second parts was (total volume 50 μl): 10 μl of 5×buffer, 2 μl of dNTP, 1 μl of specific forward and reverse primers each, 1 μl of template (the above synthetic fragment 1 or 2), and 0.5 μl of Phusion enzyme (PCR fidelity enzyme), adjusted to 50 μl with double distilled water. The reaction condition was as follows: initial denaturation at 98° C. for 30 s, followed by 10 cycles of 98° C. for 10 s and 68° C. for 2 min, followed by 30 cycles of 98° C. for 10 s, 55° C. for 30 s, and 72° C. for 50 s, and finally 72° C. for 5 min. Particularly, for kh02, the primers for the first part were P1 and P6, the template was synthetic fragment 1; the primers for the second part were P5 and P2, the template was synthetic fragment 2. For kh03, the primers for the first part were P1 and P8, the template was synthetic fragment 1; the primers for the second part were P7 and P2, the template was synthetic fragment 2. For kh04, the primers for the first part were P1 and P10, the template was synthetic fragment 1; the primers for the second part were P9 and P2, the template was synthetic fragment 2. For the coding sequence of protein KH01 (kh01), the primers for the first part were P1 and P4, the template was synthetic fragment 1; the primers for the second part were P3 and P2, the template was synthetic fragment 2. The gene products were tested by agarose gel electrophoresis. A total of 8 fragments, i.e. kh01-Q, kh01-H, kh02-Q, kh02-H, kh03-Q, kh03-H, kh04-Q and kh04-H, were obtained. The reaction system for overlapping PCR was (total volume 50 μl): 10 μl of 5×buffer, 2 μl of dNTP, 1 μl of the above amplified first and second fragment as template respectively (for example, for amplification of the full length of kh01, 1 μl of kh01-Q PCR recovery product and 1 μl of kh01-H PCR recovery product were used), 1 μl of forward and reverse primers (P1, P2) respectively, and 0.5 μl of Phusion enzyme (PCR fidelity enzyme), adjusted to 50 μl with double distilled water. The reaction condition was as follows: initial denaturation at 98° C. for 30 s, followed by 30 cycles of 98° C. for 10 s, 55° C. for 30 s, and 72° C. for 50 s, and finally 72° C. for 5 min. The gene products were tested by agarose gel electrophoresis (IQ300, GE). A total of 4 gene fragments, named as kh01-1 (corresponding to SEQ ID NO: 11, but with additional signal peptide encoding sequence), kh02-1 (corresponding to SEQ ID NO: 13, but with additional signal peptide encoding sequence), kh03-1 (corresponding to SEQ ID NO: 15, but with additional signal peptide encoding sequence), and kh04-1 (corresponding to SEQ ID NO: 17, but with additional signal peptide encoding sequence), were obtained. The amplified fragments were found to have the expected size by electrophoresis.

1.3 Enzyme Digestion of Vectors and Gene Fragments pCHO1.0 plasmid (from Life Technologies, catalog no.: A13696-01), kh01-1, kh02-1, kh03-1, and kh04-1 were subjected to double enzyme digestion respectively. The system for enzyme digestion was as follows. 40 μl of pCHO1.0 plasmid or kh01-1, kh02-1, kh03-1, or kh04-1 amplified fragment, 10 μl of 10×buffer 4 (NEB), 5 μl of AvrII (R0174L, NEB) and BstZ17I (R0594L, NEB) each, and 45 μl sterile water were added to 1.5 ml EP tube, and the mixture was incubated at 37° C. for 5 h after being mixed evenly. The product was recovered by PCR product purification kit (CAT: 28106, QIAGEN).

1.4 Ligation and Transformation of Recombinant Plasmid

The recovered pCHO1.0 fragment (larger fragment obtained by AvrII and BstZ17I digestion, about 13 kb) and the recovered kh01-1, kh02-1, kh03-1, or kh04-1 fragment (AvrII and BstZ17I digested), obtained from digestion by the same enzymes, were ligated together in the presence of T4 DNA ligase. The reaction system for this reaction was as follows. 2 μl of pCHO1.0 fragment (AvrII and BstZ17I digested), 6 μl of kh01-1, kh02-1, kh03-1, or kh04-1 (AvrII and BstZ17I digested) fragment, 1 μl of 10×T4 buffer (B0202S, NEB), and 1 μl of T4 DNA ligase (M0202L, NEB) were added to 1.5 ml EP tube, the mixture was mixed evenly, and then incubated at room temperature (around 20° C.) for 4 h. The ligation product was transformed to competent Top 10 E. coli cell (CB104, TIANGEN) and plated on 2YT (KAN) plate (Shanghai Ruicong Laboratory Equipment Co., Ltd) for overnight incubation at 37° C. The plates were identified as kh01, kh02, kh03, and kh04.

1.5 Colony PCR Screening of Recombinant Plasmids.

Single recombinant colonies were picked from kh01, kh02, kh03, and kh04 plates and were incubated at 37° C. for 3-5 h. After incubation, these colonies were used as PCR templates for PCR screening. The reaction system (total volume 20 μl) for this PCR amplification was as follows. 10 μL of 2×Taq HS (R013A, TAKATA), 2 μL of bacterial liquid as template, and 1 μL of forward primer and reserve primer (P1 and P2, each has a final concentration 0.3 μmol/L), adjusted to 20 μL with double distilled water. The condition for the reaction was: 94° C. for 3 min, followed by 30 cycles of 94° C. for 60 s, 53° C. for 60 s, and 72° C. for 120 s, and finally 72° C. for 5 min. The results showed that a target band of about 1.6 Kbp was amplified from all colonies, suggesting that these colonies are all positive clones.

1.6 Identification of Recombinant Plasmid by Enzymatic Digestion.

The colonies identified as positive by the colony PCR were inoculated, followed by plasmid extraction and identification by enzymatic digestion. Firstly, plasmids were extracted from recombinant bacteria and then analysed by enzymatic digestion. The system for enzymatic digestion was as follows. 2 μl of Plasmid, 1 μl of 10×buffer 4, 1 μl of AvrII and 1 μl of BstZ17I were added to 1.5 ml EP tube, and sterile water was added to adjust the total volume to 10 μl, and then the mixture was mixed evenly and then reacted at 37° C. for 4 h. Agarose gel electrophoresis confirmed that a band around 1.6 kb was obtained after enzymatic digestion for all colonies, suggesting that the picked clones are all positive clones.

1.7 Identification of Recombinant Plasmid by Sequencing

Colonies identified by the colony PCR and enzymatic digestion as positive were sequenced (Suzhou GENEWIZ biotech Co. Ltd.). The results of the sequencing were as expected. These expression plasmids were stored for further usage. Clones with positive sequencing results were numbered as the following, kh01-1 as 610, kh02-1 as 711, kh03-1 as 812, kh04-1 as 915.

2. Transfection of Plasmid and Screening of Cells

Transfection was conducted using host cell CHO-S in Freedom™ CHO-S™ Kit (A13696-01, LIFE TECHNOLOGIES) as suggested by the manufacturer. Four plasmids were transfected in this experiment: 610, 915, 812, and 711. Cells transfected with plasmids were incubated by shake-flask culturing. The culture was performed in CD FortiCHO (from Life Technologies) as the culture medium under 37° C., 8% $CO_2$, and 110 rpm/min for 48 h. Viability and count of the cells were detected by cell counter.

48 hours after the transfection, the two-phase selection scheme was conducted: 10P/100M, 20P/200M (P=10 μg/mL puromysin, M=nM methotrexate (MTX)); 30P/500M, 50P/1000M, with CD-FortiCHO being used as the culture medium. Cells obtained after the first screening were 610, 915, 812 and 711 (i.e., comprising the above respective plasmid). The single clone screening was performed at a seeding density of 500 viable cells/ml, and 48 hour after the transfection, each cell pool was seeded to 8 six-well plates and incubated for 1 week in incubator. The growth of cell clone in each plate was observed under fluorescence microscope. Single clone was picked by Clone Pix FL (Genetix). Protein expression and purity were detected to select clone for scale-up culture.

3. Expression, Purification and Identification of Proteins

Clone cells with high yield were picked for scale-up culture from 96-well plate to 24-well plate, then to 6-well plate and then to 50 ml shake-flask.

Supernatant of cell culture incubated for 4-6 days was collected and centrifuged to remove cell debris. The collected supernatant was filtered by 0.45 μm filter. PH was adjusted to 7.4. Fusion proteins were purified by HiTrap protein A affinity chromatography column (HiTrap protein A HP, 5×1 ml; GE). The column was rinsed by 5×deionized water, and balanced by 5×PBS buffer (20 mM phosphate, pH 7.4) (SD117-500 ml, Shanghai Biotech Co., Ltd). The column was loaded with samples and eluate was collected for detection. The column was washed with ten column volume of PBS buffer (0.02 mol/L phosphate, pH 7.4) to remove non-target protein and target protein was eluted from the column by 0.1M glycine buffer (pH3). The purities of the proteins were all detected to be above 90% by SDS-PAGE (polyacrylamide gel electrophoresis).

Example 2: Analysis of Purity and Yield of the Protein

Purities of proteins in fermentation broth were detected by SEC-HPLC. Also, the expression of each protein obtained in Example 1 was detected by ForteBio bio-molecular interaction detector (Octet QKe, Pall). The results are shown in Table 1. It can be seen that the expression levels and purities of fusion proteins KH02-KH04 are better than the same of KH01 protein. Among these proteins, fusion protein KH02 is the best in terms of purity and expression level. The purity of this protein is still maintained above 80% on day 9 of the incubation without addition of nutriment.

TABLE 1

Comparison of purity of cell culture supernatant of the proteins

| Culture supernatant | Purity (%) | | Expression level (mg/L) | |
|---|---|---|---|---|
| | Day 7 | Day 9 | Day 7 | Day 9 |
| KH01 | 53.5 | 40.1 | 173.54 | 305.27 |
| KH02 | 84.3 | 83.5 | 381.85 | 578.15 |
| KH03 | 55.5 | 42.8 | 201.3 | 300.85 |
| KH04 | 61.5 | 47.7 | 136.55 | 342.10 |

Example 3: Detection of Thermal Stability of VEGF Receptor Fusion Protein (1) Detection of Tendency for Thermal Denaturation of the VEGF Receptor Fusion Protein The spacial conformation of a protein will be unfolded when the protein is subjected to heat treatment. Hydrophobic amino acid residues (such as tryptophan, tyrosine, and phenylalanine) containing aromatic group will be exposed. The degree of protein unfolding can be reflected by fluorescence intensity (IF) inside the aromatic groups. During protein unfolding, fluorescence spectrum of the internal fluorophores will change. Protein with natural structure (normally folded) has lower internal fluorescence intensity and the peak is at around 330 nm. In contrast, denatured protein has significantly increased internal fluorescence intensity and the peak will be shifted to around 350 nm. Half thermal denaturation temperature Tm can be calculated by analysing the change of internal fluorescence intensity and the shift of peak of the protein, and indirectly reflects the tendency for thermal denaturation.

The tendency for thermal denaturation of VEGF receptor fusion protein was detected by analyzer for thermal stability of protein (Optim2, Avacta). About 15 μl of each sample to be detected (1 mg/ml PBS, pH7.2, purity above 90%) was added to Optim2 reaction tube. The range for temperature scanning was set to 25° C.-95° C. Samples were incubated at each temperature point for 60 s. The data were processed by Optim2 analysis software. The results are shown in FIG. 1 and Table 2. It is shown that among the recombinant proteins expressed in Example 1, KH02 has the highest denaturation temperature, suggesting the lowest tendency for thermal denaturation. That is, KH02 has the highest thermal stability.

TABLE 2

Parameters for thermal denaturation of the VEGF receptor fusion protein

| Samples | Denaturation temperature 1 | Denaturation temperature 2 | Denaturation temperature 3 |
|---|---|---|---|
| KH01 | 43.9° C. | 61.2° C. | 71.2° C. |
| KH02 | 48.0° C. | 63.7° C. | 77.6° C. |
| KH03 | / | 63.4° C. | 76.7° C. |
| KH04 | / | 63.3° C. | 77.1° C. |

(2) Analysis of Tendency for Thermal Aggregation of the VEGF Receptor Fusion Protein Light scattering will occur when protein is exposed to UV light. In a certain range, intensity of static light scattering is linearly related to the size of the protein (10-600 KD). Detecting the intensity of light scattering SCS (Static Light Scattering) can show the change in protein size. Tendency for protein aggregation can be indirectly reflected by calculating aggregation onset temperature (Tagg) of the protein.

Figure 2:
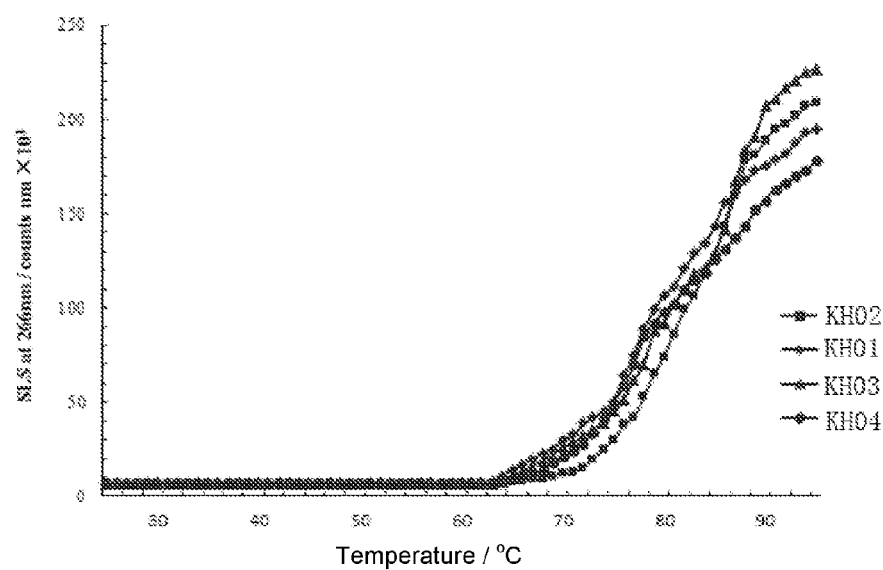
FIG. 2 is a graph showing the tendency for thermal aggregation of the VEGF receptor fusion protein. The curve in the graph reflects the change of intensity of static light scattering of the protein along with the rise of the temperature. The ordinate SLS at 266 nm shows intensity of static light scattering, while the abscissa shows the temperature.

Tendency for thermal aggregation of the VEGF receptor fusion protein was detected by analyzer for thermal stability of protein (Optim2, Avacta). About 15 µl of each sample to be detected (1 mg/ml PBS, pH7.2, purity above 90%) was added to Optim2 reaction tube. The range for temperature scanning was set to 25° C.-95° C. Samples were incubated at each temperature point for 60 s. The data were processed by Optim2 analysis software. The results are shown in FIG. 2 and Table 3. It is shown that the intensity of static light scattering increases along with the increase of temperature, and among the recombinant proteins, KH02 has the highest aggregation onset temperature (Tagg), suggesting the lowest possibility for thermal aggregation.

TABLE 3

Tendency for thermal aggregation of the VEGF receptor fusion protein

| Sample | Tagg |
| --- | --- |
| KH01 | 65.6° C. |
| KH02 | 71.8° C. |
| KH03 | 69.8° C. |
| KH04 | 68.8° C. |

Figure 3:
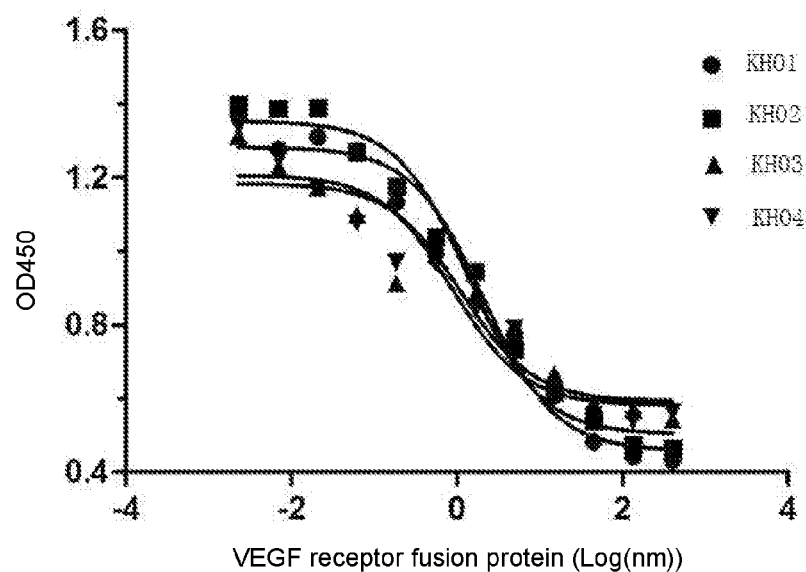
FIG. 3 is a graph showing the inhibition of VEGF-induced proliferation of HUVEC cell by the VEGF receptor fusion protein. The ordinate shows the concentration of the fusion protein, while the abscissa is absorbance showing cell viability tested by CCK-8 method.

Example 4: Detection of Biological Activities of VEGF Receptor Fusion Protein (1) Proliferation of HUVEC cell Human umbilical venous endothelial cells (HUVEC, ScienCell) that grew well were seeded to 96-well plate at $3\times10^3$ cell/well and 100 µl/well at 37° C., 5% $CO_2$ for 20 hours. ECM medium (Endothelial Cell Medium, catalog no. 1001, Sciencell) containing 2% fetal bovine serum was used to prepare VEGF receptor fusion protein with different molar concentrations (0.0023, 0.007, 0.023, 0.065, 0.19, 0.57, 1.7, 5, 15, 45, 135 nM), which was then mixed evenly with 40 ng/ml VEGF (R&D SYSTEMS), incubated for 2 h. 100 µl of the mixture was then added to HUVEC cells in 96-well plate per cell in triplet. The plate was continuously incubated with 5% $CO_2$ for 96 hours. At the end of incubation, the CCK8 (Dojindo) was added. The inhibitory effect of VEGF receptor fusion protein was shown in $EC_{50}$. The results are shown in FIG. 3 and Table 4. The present VEGF receptor fusion proteins could all inhibit the VEGF-stimulated proliferation of HUVEC cells effectively, suggesting the present VEGF receptor fusion proteins have good biological activity in terms of the inhibition of VEGF.

TABLE 4

VEGF receptor fusion proteins inhibit the VEGF-stimulated proliferation of HUVEC cells

| Sample | $EC_{50}$ (nM) |
| --- | --- |
| KH01 | 1.93 |
| KH02 | 1.26 |

TABLE 4-continued

VEGF receptor fusion proteins inhibit the VEGF-stimulated proliferation of HUVEC cells

| Sample | $EC_{50}$ (nM) |
| --- | --- |
| KH03 | 2.11 |
| KH04 | 1.43 |

(2) Migration of HUVEC Cells

Figure 4:
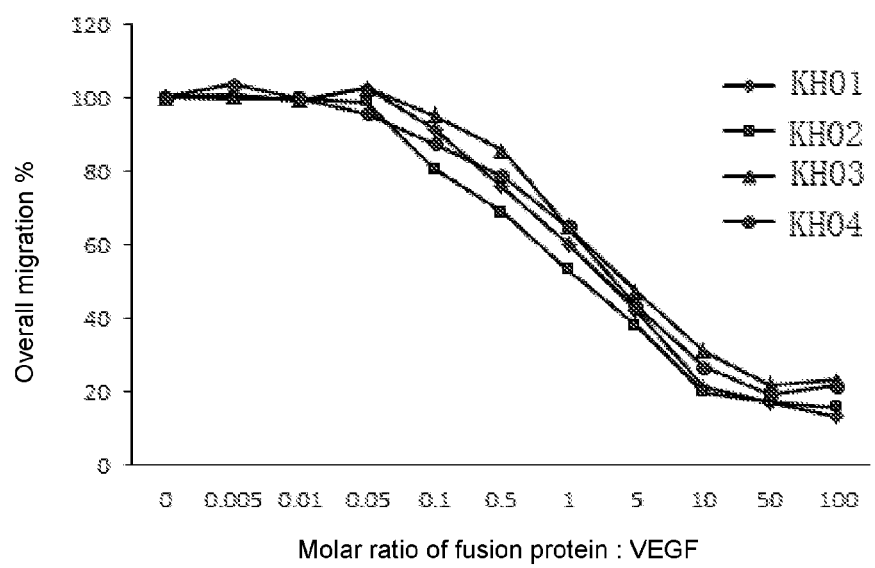
FIG. 4 is a graph showing the inhibition of VEGF-induced migration of HUVEC cell by the VEGF receptor fusion protein. The abscissa shows the molar ratio of the fusion protein to VEGF, while the ordinate is overall migration % (overall migration %=$(F_{fusion\ protein}-F_{basal})/(F_{total}-F_{basal})$, $F_{basal}$ is the mean fluorescence of culture medium group, $F_{total}$ is the mean fluorescence of VEGF group, $F_{fusion\ protein}$ is the mean fluorescence of fusion protein group with different molar ratios).

The effect of the present fusion protein on the migration of HUVEC cells was tested by using modified Boyden chamber (FluoroBlok™ Biocoat angiogenesis system: Endothelial cell migration, BD). HUVEC cells that grew well were seeded to upper compartment of the Boyden chamber at $3\times10^5$ cell/ml and 75 µl/well. ECM basic medium (catalog no. 1001, Sciencell) containing 2% fetal bovine serum was used to prepare VEGF receptor fusion protein with different molar concentrations (13333 nM, 4444 nM, 1481 nM, 494 nM, 164.5 nM, 54.8 nM, 18.3 nM, 6.1 nM), which was then mixed evenly with 500 µM VEGF (R&D SYSTEMS), incubated for 2 h, and then added to the lower compartment-of the Boyden chamber at 225 µl/well. The whole chamber was incubated at 37° C., 5% $CO_2$ for 20-24 h. The culture medium in the lower compartment was removed. Fluorescent dye Calcein AM (Anaspec) with a final concentration of 5 µg/ml formulated by using HBSS buffer (Hanks Balanced Salt Solution) was added. The chamber was incubated at 37° C. with 5% $CO_2$ for 90 minutes in the dark, and then the fluorescence value was detected at excitation wavelength of 494 nm and detection wavelength of 517 nm on a multi-mode reader. Relative migration of the cells was calculated. As shown in FIG. 4, VEGF receptor fusion proteins of the present invention are substantially the same in the inhibition of VEGF induced migration of HUVEC cells. This confirms again that fusion protein KH02 of the present invention has better biological activity in terms of the inhibition of VEGF.

Example 5: Test of Binding Affinity Between VEGF Receptor Fusion Protein and VEGF The binding affinity between human VEGF receptor fusion protein and human VEGF was detected on ForteBio bio-molecular interaction detector (Octet QKe, Pall) by Biolayer-Interferometry (BLI). Human VEGF (catalog no. 293-VE-010, R&D SYSTEMS) and NHS-LCLC-biotin (catalog no. 21338, Thermo) were mixed evenly at 1:3 molar ratio, and placed at room temperature for 1 h, then the remaining NHS-LCLC-biotin was removed, giving the final labelled product biotin-hVEGF at 50 µg/ml. 50 µg/ml biotin-hVEGF was loaded on streptavidin sensor. Samples to be tested were formulated to different concentrations (600 nM, 200 nM, 66.7 nm, 22.2 nM, 7.4 nm, 2.46 nM, 0.82 nM, respectively) by sample diluting buffer (PBS, 0.1% BSA, 0.02% Tween-20, 0.003% $NaN_3$). The sample diluting buffer was served as blank control. Parameters for binding kinetics between hVEGF and receptor fusion protein were detected under kinetics analysis mode. The results are shown in Table 5. It is shown that the VEGF receptor fusion proteins expressed in Example 1 all bind significantly with human VEGF. Among these proteins, the KD value of KH02 is about 0.33 nM. Especially, the dynamic dissociation rate of KH02 complex with VEGF is lower than other fusion proteins, suggesting the highest binding affinity.

TABLE 5

Parameters for binding affinity between VEGF receptor fusion protein and human VEGF

| | KD (nM) | kon (1/Ms) | kdis (1/s) |
|---|---|---|---|
| KH01 | 0.51 ± 0.04 | 6.91 ± 0.09 × $10^4$ | 3.53 ± 0.06 × $10^{-5}$ |
| KH02 | 0.33 ± 0.02 | 5.16 ± 0.05 × $10^4$ | 1.70 ± 0.05 × $10^{-5}$ |
| KH03 | 1.17 ± 0.05 | 8.67 ± 0.02 × $10^4$ | 1.01 ± 0.04 × $10^{-4}$ |
| KH04 | 0.35 ± 0.02 | 2.06 ± 0.05 × $10^5$ | 7.27 ± 0.02 × $10^{-5}$ |

Notes:
Kon: association constant,
Kids: dissociation constant

Example 6: Affinity Experiment of Fusion Proteins 1.1 Reagents

TABLE 6 list of the reagents used

| Name | Manufacturer | Catalog no. | Lot No. |
|---|---|---|---|
| rhVEGF165 | R&D Systems Inc. | 293-VE | II4113062 |
| Human IgG-Fc antibody HRP | BETHYL Corp. | A80-104P | A80-104P-78 |
| TMB substrate solution | R&D Systems Inc. | DY999 | 308030 |
| BSA | BOVOGEN Corp. | BSA S1.0 | 269 |
| Tween 20 | Riedel-deHaën Corp. | 63158 | 41620 |
| 20xPBS buffer | Biotech Co. | SD8117 | 13042099Z |

TABLE 7 list of instruments

| Name | Brand | Device no. |
|---|---|---|
| Microplate reader | Molecular Devices Corp. | JC084 |
| Mini vortex mixer | Shanghai LUXI Corp. | GY227 |
| Electronic balance | Sartorius Corp. | JC082 |

1.2 Protocol

1) Reagent Preparation i. 10×PBS buffer: 80.1 g of NaCl, 2.0 g of KCl, 2.0 g of $KH_2PO_4$, and 29.0 g of $Na_2HPO_4 \cdot 12H_2O$ were dissolved in pure water and the final volume was set to 1000 ml;

ii. 1×PBS buffer: 100 ml 10×PBS buffer was dissolved in 850 ml pure water, pH was adjusted to pH 7.2-7.4, and the final volume was set to 1000 ml;

iii. Carbonate buffer: 1.59 g of $Na_2CO_3$ and 2.93 g of $NaHCO_3$ were dissolved in 1000 ml ultrapure water, pH was 9.6-9.8, and the solution was stored at room temperature, and filtered with 0.22 μm filter before use.

iv. BSA (bovine serum albumin): stored at 4° C.;

v. Rinsing buffer: 1×PBS containing 0.05% (v/v) polysorbate 20;

vi. Blocking solution and diluent: 1×PBS containing 1% (w/v) BSA;

vii. Stop solution (2N $H_2SO_4$): 27.8 ml concentrated sulfuric acid was added slowly to 472.2 ml pure water. Concentrated sulfuric acid is a strong corrosive liquid and should be added with stirring by glass rod and handled with extra care;

viii. rhVEGF$_{165}$ (R&D SYSTEMS, 293-VE, 50 μg/vial) stock solution: 3 ml 1×PBS was filtered by 0.22 μm filter. 800 μl filtered PBS was added to a previously unopened vial of rhVEGF$_{165}$. When the visible solid material in the vial was dissolved, 200 μl additional filtered PBS was added. The vial was placed at room temperature for 10 min to fully dissolve rhVEGF$_{165}$. The concentration of the dissolved rhVEGF$_{165}$ stock solution was 50 μ/ml. The stock solution was divided into aliquots of 25 μl/vial. The stock solution can be stored at −20° C. for 6 months.

ix. Human IgG-Fc antibody HRP detection antibody (BETHYL A80-104P): 1 mg/ml, stored at 4° C.

2) Coating the Plate

20 μl rhVEGF$_{165}$ stock solution was added to 7980 μl carbonate buffer, the mixture was mixed evenly and named as coating solution A and its concentration was 125 ng/ml. 2500 μl coating solution A was added to 2500 μl carbonate buffer, the mixture was mixed evenly and named as coating solution B. A microplate was coated in columns 1-6 with coating solution A, and in columns 7-12 with coating solution B, wherein the volume used in the coating was 100 μl/well. The plate was sealed by sealing gel and incubated overnight at room temperature.

3) Rinsing the Plate

The plate was washed with 250 μl rinsing buffer per well and soaked for 120 s, which was repeated for three times. The remaining drops were removed by patting the plate on a paper towel until there was no obvious water mark on the paper towel.

4) Blocking the Plate

Blocking solution was added at 300 μl/well by an 8-channel pipette. Then the plate was sealed by sealing gel and incubated at 37° C. for 2 hours.

5) Preparation of Sample

Samples (fusion proteins KH02 and KH05) were diluted to 1600 ng/ml according to initial protein concentration. The volume of the 1600 ng/ml sample should be at least above 800 μl. A 4× serial dilution was conducted by adding 600 μl diluting solution to 200 μl sample, and such a diluting operation was repeated in series to obtain 8 different concentration gradients (including 1600 ng/ml).

6) Adding the Sample

The plate was rinsed as described above. 100 μl/well samples were added to microplate successively and the plate was sealed by sealing gel. The loading was proceeded from high concentration to low concentration in duplicate. After the loading, the plate was incubated at 37° C. for 1 h.

7) Adding Test Antibody

The plate was rinsed as described above. Human IgG-Fc antibody HRP 0.5 μl was diluted by 10 ml blocking solution and the mixture was mixed evenly. 100 μl/well diluted test antibody was added to wells, and the plate was incubated at 37° C. for 1 h. 8) Color Development The plate was rinsed as described above. 100 μl/well TMB substrate solution was added. The plate was incubated under dark and at room temperature for 5 min.

9) Stopping and Obtaining Readout

50 μl/well stop solution was added and the reaction was terminated. The microplate was placed under microplate reader to get a readout under 450 nm.

1.3 Results of Affinity Test

TABLE 8

Results of affinity test of samples

| Sample | treatment | Kd (unit: pM) |
|---|---|---|
| KH05 | Day 0 | 27.253 |
| | 5 days at high | 65.471 |

TABLE 8-continued

Results of affinity test of samples

| Sample | treatment | Kd (unit: pM) |
|---|---|---|
| | temperature | |
| | 10 days at high temperature | 174.983 |
| KH02 | Day 0 | 22.491 |
| | 5 days at high temperature | 46.420 |
| | 10 days at high temperature | 70.504 |

From the results in Table 8, it can be seen that the affinity of KH02 after a 10-day high temperature treatment is still within acceptable range (22-84 pM). However, affinity of KH05 after a 10-day high temperature treatment exceeds far beyond the acceptable range. Thus, the stability of KH02 in terms of activity is better than KH05.

Example 7: Purity Test at High Temperature 1.1 Reagents and Devices

TABLE 9 list of reagents used

| Name | Catalog No. | Specification | Manufacturer |
|---|---|---|---|
| $Na_2HPO_4 \cdot 12H_2O$ | 20130527 | 500 g/vial | Guangdong Guanhua Corp. |
| NaCl | 201100905 | 500 g/vial | Guangdong Guanhua Corp. |
| Arg-HCl | 20110318 | N/A | Shanghai Yuanju Biotech Corp. |
| Concentrated HCl | 20121101 | N/A | Chengdu Kelong Corp. |
| Chromatographic column | S0534 | TSK G3000 SWxl, 5 μm, 7.8 × 300 mm | TOSOH Corp. |
| TSK guard column | R1479 | 40 * 60 | TOSOH Corp. |

TABLE 10 list of main devices used

| Name | Device No. | Manufacturer | Pattern No. |
|---|---|---|---|
| High performance liquid spectrometry | JC073 | Agilent Technologies Inc. | 1200 |
| Mini vortex mixer | GY265 | Shanghai LUXI Corp. | WH-3 |
| Electronic balance | JC080 | Sartorius Corp. | BS224S |

TABLE 10-continued list of main devices used

| Name | Device No. | Manufacturer | Pattern No. |
|---|---|---|---|
| pH meter | JC077 | METTLER Corp. | TOLEDO S40K |

1.2 Protocol
1) Reagent Preparation
  i. PBS mobile phase: 7.16 g $Na_2HPO_4.12H_2O$, 8.77 g NaCl and 42.2 g Arg were dissolved in 800 ml ultrapure water, the pH was adjusted to pH7.2 by HCl, the final volume was set to 1000 ml and the resulting solution was filtered by Φ0.22 μm filter.
  ii. Guarding solution for chromatographic column (0.05% $NaN_3$): $NaN_3$ 0.5 g was dissolved in 1000 ml ultrapure water and the resulting solution was filtered by Φ0.22 μm filter.
  iii. Ultrapure water: it was filtered by Φ0.22 μm filter.
2) Preparation of Sample
Since the concentration of each sample (KH02, KH05) was 1 mg/ml, these samples can be loaded directly.
3) Conditions for Chromatographic Analysis
Mobile phase: PBS mobile phase;
Chromatographic column: TSK G3000 $SW_{XL}$ (5 μm, 7.8*300 mm);
Temperature of the column: 25° C.; flow rate: 0.5 ml/min; detection wavelength: 280 nm; loading volume: 50 μl.
1.3 Results

TABLE 11

Results of SEC-HPLC purity test of the samples

| Sample | Treatment | Detected purity (%) |
|---|---|---|
| KH05 | Day 0 | 99.19 |
| | 5 days at high temperature | 54.06 |
| | 10 days at high temperature | 25.20 |
| KH02 | Day 0 | 96.75 |
| | 5 days at high temperature | 94.29 |
| | 10 days at high temperature | 65.15 |

As can be seen from Table 11, the purity of KH05 dropped to 54% after a 5-day high temperature treatment. The purity of KH05 was only 25% after a 10-day high temperature treatment. The decrease of purity of KH02 was inapparent after a 5-day high temperature treatment. The purity of KH02 sample was up to 65% after a 10-day high temperature treatment.

The invention claimed is:

1. A fusion protein for the inhibition of angiogenesis or vascular growth, the fusion protein comprising a human VEGF receptor fragment and an Fc fragment of human immunoglobulin linked thereto, wherein the amino acid sequence of the VEGF receptor fragment is SEQ ID NO: 1, SEQ ID NO: 3 or SEQ ID NO: 5, and wherein the fusion protein is
    KH02, the amino acid sequence of which is as shown in SEQ ID NO: 14;
    KH03, the amino acid sequence of which is as shown in SEQ ID NO: 16; or
    KH04, the amino acid sequence of which is as shown in SEQ ID NO: 18.

2. A nucleotide sequence encoding the fusion protein according to claim 1.

3. The nucleotide sequence of claim 2, wherein the nucleotide sequence is the sequence shown in SEQ ID NO: 13, SEQ ID NO: 15 or SEQ ID NO: 17.

4. An expression vector comprising a nucleotide sequence encoding the fusion protein according to claim 1.

5. The expression vector according to claim 4, wherein, the expression vector is a eukaryotic expression vector or a viral expression vector.

6. The expression vector according to claim 5, wherein, the expression vector is a mammalian cell expression vector or adeno-associated virus vector or adenovirus vector.

7. A pharmaceutical composition comprising the fusion protein according to claim 1 and pharmaceutically acceptable carrier or excipient.

8. A method for treating a disease caused by angiogenesis or vascular growth, the method comprising administering the pharmaceutical composition of claim 7 to a patient in need thereof to inhibit angiogenesis or vascular growth.

9. The method for treating disease caused by angiogenesis or vascular growth according to claim 8, wherein the disease caused by angiogenesis or vascular growth is selected from the group consisting of tumor, age-related macular degeneration, diabetic retinopathy, and chorioretinopathy.

10. The pharmaceutical composition according to claim 7, in the form of a formulation for injection, a freeze-dried injection powder, or an ophthalmic gel.

11. A host cell comprising a nucleotide sequence encoding the fusion protein according to claim 1.

12. The host cell according to claim 11, wherein, the host cell is a CHO cell or a 293 cell.

* * * * *

SEQUENCE LISTING

```
<160> NUMBER OF SEQ ID NOS: 32

<210> SEQ ID NO 1
<211> LENGTH: 296
<212> TYPE: PRT
<213> ORGANISM: Homo sapiens

<400> SEQUENCE: 1

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30
```

-continued

```
Asn Ile Thr Val Thr Leu Lys Lys Phe Pro Leu Asp Thr Leu Ile Pro
         35                  40                  45

Asp Gly Lys Arg Ile Ile Trp Asp Ser Arg Lys Gly Phe Ile Ile Ser
     50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                 85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Arg Val Tyr Val Pro Pro
    290                 295
```

<210> SEQ ID NO 2
<211> LENGTH: 888
<212> TYPE: DNA
<213> ORGANISM: Homo sapiens

<400> SEQUENCE: 2

```
ggtagacctt tcgtagagat gtacagtgaa atccccgaaa ttatacacat gactgaagga    60
agggagctcg tcattccctg ccgggttacg tcacctaaca tcactgttac tttaaaaaag   120
tttccacttg acactttgat ccctgatgga aaacgcataa tctgggacag tagaaagggc   180
ttcatcatat caaatgcaac gtacaaagaa atagggcttc tgacctgtga agcaacagtc   240
aatgggcatt tgtataagac aaactatctc acacatcgac aaaccaatac aatcatagat   300
gtggttctga gtccgtctca tggaattgaa ctatctgttg gagaaaagct tgtcttaaat   360
tgtacagcaa gaactgaact aaatgtgggg attgacttca ctgggaata cccttcttcg   420 aagcatcagc ataagaaact tgtaaaccga gacctaaaaa cccagtctgg gagtgagatg   480
aagaaatttt tgagcacctt aactatagat ggtgtaaccc ggagtgacca aggattgtac   540
acctgtgcag catccagtgg gctgatgacc aagaagaaca gcacatttgt cagggtccat   600
```

```
gaaaaacctt tgttgctttt tggaagtggc atggaatctc tggtggaagc cacggtgggg    660
gagcgtgtca gaatccctgc gaagtacctt ggttacccac ccccagaaat aaaatggtat    720
aaaaatggaa taccccttga gtccaatcac acaattaaag cggggcatgt actgacgatt    780
atggaagtga gtgaaagaga cacaggaaat tacactgtca tccttaccaa tcccatttca    840
aaggagaagc agagccatgt ggtctctctg cgtgtgtatg tcccaccg                 888
```

<210> SEQ ID NO 3
<211> LENGTH: 296
<212> TYPE: PRT
<213> ORGANISM: Homo sapiens

<400> SEQUENCE: 3

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Pro Val Tyr Val Pro Pro
    290                 295
```

<210> SEQ ID NO 4
<211> LENGTH: 888

<212> TYPE: DNA
<213> ORGANISM: Homo sapiens

<400> SEQUENCE: 4

```
ggtagacctt tcgtagagat gtacagtgaa atccccgaaa ttatacacat gactgaagga      60
agggagctcg tcattccctg ccgggttacg tcacctaaca tcactgttac tttaaaaaag     120
tttccacttg acactttgat ccctgatgga aaacgcataa tctgggacag tagaaagggc     180
ttcatcatat caaatgcaac gtacaaagaa atagggcttc tgacctgtga agcaacagtc     240
aatgggcatt tgtataagac aaactatctc acacatcgac aaaccaatac aatcatagat     300
gtggttctga gtccgtctca tggaattgaa ctatctgttg gagaaaagct tgtcttaaat     360
tgtacagcaa gaactgaact aaatgtgggg attgacttca actgggaata cccttcttcg     420
aagcatcagc ataagaaact tgtaaaccga gacctaaaaa cccagtctgg gagtgagatg     480
aagaaatttt tgagcacctt aactatagat ggtgtaaccc ggagtgacca aggattgtac     540
acctgtgcag catccagtgg gctgatgacc aagaagaaca gcacatttgt cagggtccat     600
gaaaaacctt tgttgctttt ggaagtggc atggaatctc tggtggaagc cacggtgggg     660
gagcgtgtca gaatccctgc gaagtacctt ggttacccac ccccagaaat aaaatggtat     720
aaaaatggaa taccccttga gtccaatcac acaattaaag cggggcatgt actgacgatt     780
atggaagtga gtgaaagaga cacaggaaat tacactgtca tccttaccaa tcccatttca     840
aaggagaagc agagccatgt ggtctctctg cctgtgtatg tcccaccg               888
```

<210> SEQ ID NO 5
<211> LENGTH: 296
<212> TYPE: PRT
<213> ORGANISM: Homo sapiens

<400> SEQUENCE: 5

```
Gly Arg Pro Phe Val Glu Met Tyr Ser Glu Ile Pro Glu Ile Ile His
1               5                   10                  15
Met Thr Glu Gly Arg Glu Leu Val Ile Pro Cys Arg Val Thr Ser Pro
            20                  25                  30
Asn Ile Thr Val Thr Leu Lys Lys Phe Pro Leu Asp Thr Leu Ile Pro
        35                  40                  45
Asp Gly Lys Arg Ile Ile Trp Asp Ser Arg Lys Gly Phe Ile Ile Ser
    50                  55                  60
Asn Ala Thr Tyr Lys Glu Ile Gly Leu Leu Thr Cys Glu Ala Thr Val
65                  70                  75                  80
Asn Gly His Leu Tyr Lys Thr Asn Tyr Leu Thr His Arg Gln Thr Asn
                85                  90                  95
Thr Ile Ile Asp Val Val Leu Ser Pro Ser His Gly Ile Glu Leu Ser
            100                 105                 110
Val Gly Glu Lys Leu Val Leu Asn Cys Thr Ala Arg Thr Glu Leu Asn
        115                 120                 125
Val Gly Ile Asp Phe Asn Trp Glu Tyr Pro Ser Ser Lys His Gln His
    130                 135                 140
Lys Lys Leu Val Asn Arg Asp Leu Lys Thr Gln Ser Gly Ser Glu Met
145                 150                 155                 160
Lys Lys Phe Leu Ser Thr Leu Thr Ile Asp Gly Val Thr Arg Ser Asp
                165                 170                 175
Gln Gly Leu Tyr Thr Cys Ala Ala Ser Ser Gly Leu Met Thr Lys Lys
            180                 185                 190
```

Asn Ser Thr Phe Val Arg Val His Glu Lys Pro Phe Val Ala Phe Gly
            195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Arg Pro Val Tyr Val Pro Pro
    290                 295

<210> SEQ ID NO 6
<211> LENGTH: 888
<212> TYPE: DNA
<213> ORGANISM: Homo sapiens

<400> SEQUENCE: 6
ggtagacctt tcgtagagat gtacagtgaa atccccgaaa ttatacacat gactgaagga      60
agggagctcg tcattccctg ccgggttacg tcacctaaca tcactgttac tttaaaaaag     120
tttccacttg acactttgat ccctgatgga aaacgcataa tctgggacag tagaaagggc     180
ttcatcatat caaatgcaac gtacaaagaa atagggcttc tgacctgtga agcaacagtc     240
aatgggcatt tgtataagac aaactatctc acacatcgac aaaccaatac aatcatagat     300
gtggttctga gtccgtctca tggaattgaa ctatctgttg agaaaagct tgtcttaaat     360
tgtacagcaa gaactgaact aaatgtgggg attgacttca ctgggaata cccttcttcg     420
aagcatcagc ataagaaact tgtaaaccga gacctaaaaa cccagtctgg gagtgagatg     480
aagaaatttt tgagcacctt aactatagat ggtgtaaccc ggagtgacca aggattgtac     540
acctgtgcag catccagtgg gctgatgacc aagaagaaca gcacatttgt cagggtccat     600
gaaaaacctt ttgttgcttt tggaagtggc atggaatctc tggtggaagc cacggtgggg     660
gagcgtgtca gaatccctgc gaagtacctt ggttacccac cccagaaat aaaatggtat     720
aaaaatggaa tacccttga gtccaatcac acaattaaag cggggcatgt actgacgatt     780
atggaagtga gtgaaagaga cacaggaaat tacactgtca tccttaccaa tcccatttca     840
aaggagaagc agagccatgt ggtctctcgt cctgtgtatg tcccaccg                888

<210> SEQ ID NO 7
<211> LENGTH: 227
<212> TYPE: PRT
<213> ORGANISM: Homo sapiens

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 228
<212> TYPE: PRT
<213> ORGANISM: Homo sapiens

<400> SEQUENCE: 8

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 9
<211> LENGTH: 264
<212> TYPE: PRT
<213> ORGANISM: Homo sapiens

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Gln Phe Lys Trp Tyr Val
                85                  90                  95

Asp Gly Val Glu Val His Asn Ala Lys Thr Lys Pro Arg Glu Glu Gln
            100                 105                 110

Phe Asn Ser Thr Phe Arg Val Val Ser Val Leu Thr Val Leu His Gln
        115                 120                 125

Asp Trp Leu Asn Gly Lys Glu Tyr Lys Cys Lys Val Ser Asn Lys Ala
130                 135                 140

Leu Pro Ala Pro Ile Glu Lys Thr Ile Ser Lys Thr Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Ser Gly Gln Pro Glu Asn Asn Tyr
        195                 200                 205

Asn Thr Thr Pro Pro Met Leu Asp Ser Asp Gly Ser Phe Phe Leu Tyr
    210                 215                 220

Ser Lys Leu Thr Val Asp Lys Ser Arg Trp Gln Gln Gly Asn Ile Phe
225                 230                 235                 240

Ser Cys Ser Val Met His Glu Ala Leu His Asn Arg Phe Thr Gln Lys
                245                 250                 255

Ser Leu Ser Leu Ser Pro Gly Lys
            260

<210> SEQ ID NO 10
<211> LENGTH: 229
<212> TYPE: PRT
<213> ORGANISM: Homo sapiens

<400> SEQUENCE: 10

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

```
Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Pro Gly Lys
225

<210> SEQ ID NO 11
<211> LENGTH: 1578
<212> TYPE: DNA
<213> ORGANISM: artificial sequence
<220> FEATURE:
<223> OTHER INFORMATION: coding sequence for fusion protein KH01

<400> SEQUENCE: 11
ggtagacctt tcgtagagat gtacagtgaa atccccgaaa ttatacacat gactgaagga    60
agggagctcg tcattccctg ccgggttacg tcacctaaca tcactgttac tttaaaaaag   120
tttccacttg acactttgat ccctgatgga aaacgcataa tctgggacag tagaaagggc   180
ttcatcatat caaatgcaac gtacaaagaa atagggcttc tgacctgtga agcaacagtc   240
aatgggcatt tgtataagac aaactatctc acacatcgac aaaccaatac aatcatagat   300
gtggttctga gtccgtctca tggaattgaa ctatctgttg agaaaagct tgtcttaaat   360 tgtacagcaa gaactgaact aaatgtgggg attgacttca ctgggaata cccttcttcg   420 aagcatcagc ataagaaact tgtaaaccga gacctaaaaa cccagtctgg gagtgagatg   480
aagaaatttt tgagcaccct aactatagat ggtgtaaccc ggagtgacca aggattgtac   540
acctgtgcag catccagtgg gctgatgacc aagaagaaca gcacatttgt cagggtccat   600
gaaaaacctt tgttgctttt ggaagtggc atggaatctc tggtggaagc cacggtgggg   660
gagcgtgtca gaatccctgc gaagtacctt ggttacccac cccagaaat aaaatggtat   720 aaaaatggaa tacccttga gtccaatcac acaattaaag cggggcatgt actgacgatt   780
atggaagtga gtgaaagaga cacaggaaat tacactgtca tccttaccaa tcccatttca   840
aaggagaagc agagccatgt ggtctctctg gttgtgtatg tcccaccggg cccgggcgac   900
```

-continued

```
aaaactcaca catgcccacc gtgcccagca cctgaactcc tggggggacc gtcagtcttc    960
ctcttccccc caaaacccaa ggacaccctc atgatctccc ggacccctga ggtcacatgc   1020
gtggtggtgg acgtgagcca cgaagaccct gaggtcaagt tcaactggta cgtggacggc   1080
gtggaggtgc ataatgccaa gacaaagccg cgggaggagc agtacaacag cacgtaccgt   1140
gtggtcagcg tcctcaccgt cctgcaccag gactggctga atggcaagga gtacaagtgc   1200
aaggtctcca acaaagccct cccagccccc atcgagaaaa ccatctccaa agccaaaggg   1260
cagccccgag aaccacaggt gtacaccctg cccccatccc gggatgagct gaccaagaac   1320
caggtcagcc tgacctgcct ggtcaaaggc ttctatccca gcgacatcgc cgtggagtgg   1380
gagagcaatg ggcagccgga gaacaactac aagaccacgc ctcccgtgct ggactccgac   1440
ggctccttct tcctctatag caagctcacc gtggacaaga gcaggtggca gcaggggaac   1500
gtcttctcat gctccgtgat gcatgaggct ctgcacaacc actacacgca gaagagcctc   1560
tccctgtctc cgggtaaa                                                 1578
```

<210> SEQ ID NO 12
<211> LENGTH: 526
<212> TYPE: PRT
<213> ORGANISM: artificial sequence
<220> FEATURE:
<223> OTHER INFORMATION: fusion protein KH01

<400> SEQUENCE: 12

```
Gly Arg Pro Phe Val Glu Met Tyr Ser Glu Ile Pro Glu Ile Ile His
1               5                  10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240
```

Lys Asn Gly Ile Pro Leu Glu Ser Asn His Thr Ile Lys Ala Gly His
            245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
            275                 280                 285

Ser Leu Val Val Tyr Val Pro Pro Gly Pro Gly Asp Lys Thr His Thr
            290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
            325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
            355                 360                 365

Lys Pro Arg Glu Glu Gln Tyr Asn Ser Thr Tyr Arg Val Val Ser Val
            370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
            405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
            435                 440                 445

Lys Gly Phe Tyr Pro Ser Asp Ile Ala Val Glu Trp Glu Ser Asn Gly
            450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
            485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys
            515                 520                 525

<210> SEQ ID NO 13
<211> LENGTH: 1578
<212> TYPE: DNA
<213> ORGANISM: artificial sequence
<220> FEATURE:
<223> OTHER INFORMATION: coding sequence for fusion protein KH02

<400> SEQUENCE: 13
ggtagacctt tcgtagagat gtacagtgaa atccccgaaa ttatacacat gactgaagga      60
agggagctcg tcattccctg ccgggttacg tcacctaaca tcactgttac tttaaaaaag     120
tttccacttg acactttgat ccctgatgga aaacgcataa tctgggacag tagaaagggc     180
ttcatcatat caaatgcaac gtacaaagaa atagggcttc tgacctgtga agcaacagtc     240
aatgggcatt tgtataagac aaactatctc acacatcgac aaaccaatac aatcatagat     300
gtggttctga gtccgtctca tggaattgaa ctatctgttg agaaaagct tgtcttaaat     360 tgtacagcaa gaactgaact aaatgtgggg attgacttca ctgggaata cccttcttcg     420

```
aagcatcagc ataagaaact tgtaaaccga gacctaaaaa cccagtctgg gagtgagatg    480
aagaaatttt tgagcacctt aactatagat ggtgtaaccc ggagtgacca aggattgtac    540
acctgtgcag catccagtgg gctgatgacc aagaagaaca gcacatttgt cagggtccat    600
gaaaaacctt tgttgctttt tggaagtggc atggaatctc tggtggaagc cacggtgggg    660
gagcgtgtca gaatccctgc gaagtacctt ggttacccac cccagaaaat aaaatggtat    720
aaaaatggaa tacccttga gtccaatcac acaattaaag cggggcatgt actgacgatt    780
atggaagtga gtgaaagaga cacaggaaat tacactgtca tccttaccaa tcccatttca    840
aaggagaagc agagccatgt ggtctctctg cgtgtgtatg tcccaccggg ccgggcgac     900 aaaactcaca catgcccacc gtgcccagca cctgaactcc tggggggacc gtcagtcttc    960
ctcttccccc caaaacccaa ggacaccctc atgatctccc ggaccctga ggtcacatgc     1020 gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaagccct cccagccccc atcgagaaaa ccatctccaa agccaaaggg    1260
cagccccgag aaccacaggt gtacaccctg cccccatccc gggatgagct gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctatag caagctcacc gtggacaaga gcaggtggca gcagggggaac   1500 gtcttctcat gctccgtgat gcatgaggct ctgcacaacc actacacgca gaagagcctc    1560
tccctgtctc cgggtaaa                                                    1578
```

<210> SEQ ID NO 14
<211> LENGTH: 526
<212> TYPE: PRT
<213> ORGANISM: artificial sequence
<220> FEATURE:
<223> OTHER INFORMATION: fusion protein KH02

<400> SEQUENCE: 14

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160
```

```
Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Arg Val Tyr Val Pro Pro Gly Pro Gly Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys
        515                 520                 525

<210> SEQ ID NO 15
<211> LENGTH: 1578
<212> TYPE: DNA
<213> ORGANISM: artificial sequence
<220> FEATURE:
<223> OTHER INFORMATION: coding sequence for fusion protein KH03

<400> SEQUENCE: 15
```

-continued

```
ggtagacctt tcgtagagat gtacagtgaa atccccgaaa ttatacacat gactgaagga      60
agggagctcg tcattccctg ccgggttacg tcacctaaca tcactgttac tttaaaaaag     120
tttccacttg acactttgat ccctgatgga aaacgcataa tctgggacag tagaaagggc     180
ttcatcatat caaatgcaac gtacaaagaa atagggcttc tgacctgtga agcaacagtc     240
aatgggcatt tgtataagac aaactatctc acacatcgac aaaccaatac aatcatagat     300
gtggttctga gtccgtctca tggaattgaa ctatctgttg gagaaaagct tgtcttaaat     360
tgtacagcaa gaactgaact aaatgtgggg attgacttca actgggaata cccttcttcg     420
aagcatcagc ataagaaact tgtaaaccga gacctaaaaa cccagtctgg gagtgagatg     480
aagaaatttt tgagcacctt aactatagat ggtgtaaccc ggagtgacca aggattgtac     540
acctgtgcag catccagtgg gctgatgacc aagaagaaca gcacatttgt cagggtccat     600
gaaaaacctt tgttgctttt tggaagtggc atggaatctc tggtggaagc cacggtgggg     660
gagcgtgtca gaatccctgc gaagtacctt ggttacccac ccccagaaat aaaatggtat     720
aaaaatggaa taccccttga gtccaatcac acaattaaag cggggcatgt actgacgatt     780
atggaagtga gtgaaagaga cacaggaaat tacactgtca tccttaccaa tcccatttca     840
aaggagaagc agagccatgt ggtctctctg cctgtgtatg tcccaccggg cccgggcgac     900
aaaactcaca catgcccacc gtgcccagca cctgaactcc tggggggacc gtcagtcttc     960
ctcttccccc caaaacccaa ggacaccctc atgatctccc ggacccctga ggtcacatgc    1020
gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaagccct cccagccccc atcgagaaaa ccatctccaa agccaaaggg    1260
cagccccgag aaccacaggt gtacaccctg cccccatccc gggatgagct gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctatag caagctcacc gtggacaaga gcaggtggca gcaggggaac    1500
gtcttctcat gctccgtgat gcatgaggct ctgcacaacc actacacgca gaagagcctc    1560
tccctgtctc cgggtaaa                                                  1578
```

<210> SEQ ID NO 16
<211> LENGTH: 526
<212> TYPE: PRT
<213> ORGANISM: artificial sequence
<220> FEATURE:
<223> OTHER INFORMATION: fusion protein KH03

<400> SEQUENCE: 16

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80
```

```
Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Pro Val Tyr Val Pro Pro Gly Pro Gly Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495
```

Gln Gln Gly Asn Val Phe Ser Cys Ser Val Met His Glu Ala Leu His
            500                 505                 510

Asn His Tyr Thr Gln Lys Ser Leu Ser Leu Ser Pro Gly Lys
            515                 520                 525

<210> SEQ ID NO 17
<211> LENGTH: 1578
<212> TYPE: DNA
<213> ORGANISM: artificial sequence
<220> FEATURE:
<223> OTHER INFORMATION: coding sequence for fusion protein KH04

<400> SEQUENCE: 17

```
ggtagacctt tcgtagagat gtacagtgaa atccccgaaa ttatacacat gactgaagga      60
agggagctcg tcattccctg ccgggttacg tcacctaaca tcactgttac tttaaaaaag     120
tttccacttg acactttgat ccctgatgga aaacgcataa tctgggacag tagaaagggc     180
ttcatcatat caaatgcaac gtacaaagaa atagggcttc tgacctgtga agcaacagtc     240
aatgggcatt tgtataagac aaactatctc acacatcgac aaaccaatac aatcatagat     300
gtggttctga gtccgtctca tggaattgaa ctatctgttg agaaaagct tgtcttaaat     360 tgtacagcaa gaactgaact aaatgtgggg attgacttca actgggaata cccttcttcg     420
aagcatcagc ataagaaact tgtaaaccga gacctaaaaa cccagtctgg gagtgagatg     480
aagaaatttt tgagcacctt aactatagat ggtgtaaccc ggagtgacca aggattgtac     540
acctgtgcag catccagtgg gctgatgacc aagaagaaca gcacatttgt cagggtccat     600
gaaaaaccct tgttgctttt ggaagtggc atggaatctc tggtggaagc cacggtgggg     660
gagcgtgtca gaatccctgc gaagtacctt ggttaccacc cccagaaaat aaaatggtat     720
aaaaatggaa taccccttga gtccaatcac acaattaaag cggggcatgt actgacgatt     780
atggaagtga gtgaaagaga cacaggaaat tacactgtca tccttaccaa tcccatttca     840
aaggagaagc agagccatgt ggtctctcgt cctgtgtatg tccccaccggg cccgggcgac     900 aaaactcaca catgcccacc gtgcccagca cctgaactcc tggggggacc gtcagtcttc     960
ctcttccccc caaaacccaa ggacaccctc atgatctccc ggacccctga ggtcacatgc    1020
gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaagccct cccagccccc atcgagaaaa ccatctccaa agccaaaggg    1260
cagccccgag aaccacaggt gtacaccctg cccccatccc gggatgagct gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctatag caagctcacc gtggacaaga gcaggtggca gcaggggaac    1500
gtcttctcat gctccgtgat gcatgaggct ctgcacaacc actacacgca gaagagcctc    1560
tccctgtctc cgggtaaa                                                 1578
```

<210> SEQ ID NO 18
<211> LENGTH: 526
<212> TYPE: PRT
<213> ORGANISM: artificial sequence
<220> FEATURE:
<223> OTHER INFORMATION: fusion protein KH04

<400> SEQUENCE: 18

```
Gly Arg Pro Phe Val Glu Met Tyr Ser Glu Ile Pro Glu Ile Ile His
  1               5                  10                  15

Met Thr Glu Gly Arg Glu Leu Val Ile Pro Cys Arg Val Thr Ser Pro
             20                  25                  30

Asn Ile Thr Val Thr Leu Lys Lys Phe Pro Leu Asp Thr Leu Ile Pro
             35                  40                  45

Asp Gly Lys Arg Ile Ile Trp Asp Ser Arg Lys Gly Phe Ile Ile Ser
     50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                 85                  90                  95

Thr Ile Ile Asp Val Val Leu Ser Pro Ser His Gly Ile Glu Leu Ser
             100                 105                 110

Val Gly Glu Lys Leu Val Leu Asn Cys Thr Ala Arg Thr Glu Leu Asn
         115                 120                 125

Val Gly Ile Asp Phe Asn Trp Glu Tyr Pro Ser Ser Lys His Gln His
     130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                 165                 170                 175

Gln Gly Leu Tyr Thr Cys Ala Ala Ser Ser Gly Leu Met Thr Lys Lys
             180                 185                 190

Asn Ser Thr Phe Val Arg Val His Glu Lys Pro Phe Val Ala Phe Gly
         195                 200                 205

Ser Gly Met Glu Ser Leu Val Glu Ala Thr Val Gly Glu Arg Val Arg
     210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                 245                 250                 255

Val Leu Thr Ile Met Glu Val Ser Glu Arg Asp Thr Gly Asn Tyr Thr
             260                 265                 270

Val Ile Leu Thr Asn Pro Ile Ser Lys Glu Lys Gln Ser His Val Val
         275                 280                 285

Ser Arg Pro Val Tyr Val Pro Pro Gly Pro Gly Asp Lys Thr His Thr
     290                 295                 300

Cys Pro Pro Cys Pro Ala Pro Glu Leu Leu Gly Pro Ser Val Phe
305                 310                 315                 320

Leu Phe Pro Pro Lys Pro Lys Asp Thr Leu Met Ile Ser Arg Thr Pro
                 325                 330                 335

Glu Val Thr Cys Val Val Val Asp Val Ser His Glu Asp Pro Glu Val
             340                 345                 350

Lys Phe Asn Trp Tyr Val Asp Gly Val Glu Val His Asn Ala Lys Thr
         355                 360                 365

Lys Pro Arg Glu Glu Gln Tyr Asn Ser Thr Tyr Arg Val Val Ser Val
     370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                 405                 410                 415
```

| | | | | | | | | | | | |
|---|---|---|---|---|---|---|---|---|---|---|---|
|Lys|Ala|Lys|Gly|Gln|Pro|Arg|Glu|Pro|Gln|Val|Tyr|Thr|Leu|Pro|Pro|
| | | |420| | | |425| | | |430|

| | | | | | | | | | | | |
|---|---|---|---|---|---|---|---|---|---|---|---|
|Ser|Arg|Asp|Glu|Leu|Thr|Lys|Asn|Gln|Val|Ser|Leu|Thr|Cys|Leu|Val|
| | |435| | | |440| | | |445|

| | | | | | | | | | | | |
|---|---|---|---|---|---|---|---|---|---|---|---|
|Lys|Gly|Phe|Tyr|Pro|Ser|Asp|Ile|Ala|Val|Glu|Trp|Glu|Ser|Asn|Gly|
| |450| | | |455| | | |460|

| | | | | | | | | | | | |
|---|---|---|---|---|---|---|---|---|---|---|---|
|Gln|Pro|Glu|Asn|Asn|Tyr|Lys|Thr|Thr|Pro|Pro|Val|Leu|Asp|Ser|Asp|
|465| | | |470| | | |475| | | |480|

| | | | | | | | | | | | |
|---|---|---|---|---|---|---|---|---|---|---|---|
|Gly|Ser|Phe|Phe|Leu|Tyr|Ser|Lys|Leu|Thr|Val|Asp|Lys|Ser|Arg|Trp|
| | | |485| | | |490| | | |495|

| | | | | | | | | | | | |
|---|---|---|---|---|---|---|---|---|---|---|---|
|Gln|Gln|Gly|Asn|Val|Phe|Ser|Cys|Ser|Val|Met|His|Glu|Ala|Leu|His|
| | |500| | | |505| | | |510|

| | | | | | | | | | | |
|---|---|---|---|---|---|---|---|---|---|---|
|Asn|His|Tyr|Thr|Gln|Lys|Ser|Leu|Ser|Leu|Ser|Pro|Gly|Lys|
| | |515| | | |520| | | |525|

<210> SEQ ID NO 19
<211> LENGTH: 1578
<212> TYPE: DNA
<213> ORGANISM: artificial sequence
<220> FEATURE:
<223> OTHER INFORMATION: coding sequence for fusion protein KH05

<400> SEQUENCE: 19

| | | | | | |
|---|---|---|---|---|---|
|ggtagacctt|tcgtagagat|gtacagtgaa|atccccgaaa|ttatacacat|gactgaagga|60|
|agggagctcg|tcattccctg|ccgggttacg|tcacctaaca|tcactgttac|tttaaaaaag|120|
|tttccacttg|acactttgat|ccctgatgga|aaacgcataa|tctgggacag|tagaaagggc|180|
|ttcatcatat|caaatgcaac|gtacaaagaa|atagggcttc|tgacctgtga|agcaacagtc|240|
|aatgggcatt|gtataagac|aaactatctc|acacatcgac|aaaccaatac|aatcatagat|300|
|gtggttctga|gtccgtctca|tggaattgaa|ctatctgttg|agaaaagct|tgtcttaaat|360|
|tgtacagcaa|gaactgaact|aaatgtgggg|attgacttca|actgggaata|cccttcttcg|420|
|aagcatcagc|ataagaaact|tgtaaaccga|gacctaaaaa|cccagtctgg|gagtgagatg|480|
|aagaaatttt|tgagcacctt|aactatagat|ggtgtaaccc|ggagtgacca|aggattgtac|540|
|acctgtgcag|catccagtgg|gctgatgacc|aagaagaaca|gcacatttgt|cagggtccat|600|
|gaaaaccttt|ctgttgcttt|tggaagtggc|atggaatctc|tggtggaagc|cacggtgggg|660|
|gagcgtgtca|gaatccctgc|gaagtacctt|ggttacccac|cccagaaaat|aaaatggtat|720|
|aaaaatggaa|tacccttga|gtccaatcac|acaattaaag|cggggcatgt|actgacgatt|780|
|atggaagtga|gtgaaagaga|cacaggaaat|tacactgtca|tccttaccaa|tcccatttca|840|
|aaggagaagc|agagccatgt|ggtctctctg|gttgtgtatg|tcccaccggg|cccgggcgac|900|
|aaaactcaca|catgcccact|gtgcccagca|cctgaactcc|tggggggacc|gtcagtcttc|960|
|ctcttcccc|caaaacccaa|ggacaccctc|atgatctccc|ggacccctga|ggtcacatgc|1020|
|gtggtggtgg|acgtgagcca|cgaagaccct|gaggtcaagt|tcaactggta|cgtggacggc|1080|
|gtggaggtgc|ataatgccaa|gacaaagccg|cgggaggagc|agtacaacag|cacgtaccgt|1140|
|gtggtcagcg|tcctcaccgt|cctgcaccag|gactggctga|atggcaagga|gtacaagtgc|1200|
|aaggtctcca|acaaagccct|cccagccccc|atcgagaaaa|ccatctccaa|agccaaaggg|1260|
|cagccccgag|aaccacaggt|gtacaccctg|cccccatccc|gggatgagct|gaccaagaac|1320|
|caggtcagcc|tgacctgcct|agtcaaaggc|ttctatccca|gcgacatcgc|cgtggagtgg|1380|
|gagagcaatg|ggcagccgga|gaacaactac|aaggccacgc|ctcccgtgct|ggactccgac|1440|

```
ggctccttct tcctctacag caagctcacc gtggacaaga gcaggtggca gcagggaac      1500 gtcttctcat gctccgtgat gcatgaggct ctgcacaacc actacacgca gaagagcctc      1560
tccctgtctc cgggtaaa                                                    1578
```

<210> SEQ ID NO 20
<211> LENGTH: 526
<212> TYPE: PRT
<213> ORGANISM: artificial sequence
<220> FEATURE:
<223> OTHER INFORMATION: fusion protein KH05

<400> SEQUENCE: 20

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Phe Val Ala Phe Gly
        195                 200                 205

Ser Gly Met Glu Ser Leu Val Glu Ala Thr Val Gly Glu Arg Val Arg
    210                 215                 220

Ile Pro Ala Lys Tyr Leu Gly Tyr Pro Pro Glu Ile Lys Trp Tyr
225                 230                 235                 240

Lys Asn Gly Ile Pro Leu Glu Ser Asn His Thr Ile Lys Ala Gly His
                245                 250                 255

Val Leu Thr Ile Met Glu Val Ser Glu Arg Asp Thr Gly Asn Tyr Thr
            260                 265                 270

Val Ile Leu Thr Asn Pro Ile Ser Lys Glu Lys Gln Ser His Val Val
        275                 280                 285

Ser Leu Val Val Tyr Val Pro Pro Gly Pro Gly Asp Lys Thr His Thr
    290                 295                 300

Cys Pro Leu Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335
```

```
Glu Val Thr Cys Val Val Asp Val Ser His Glu Asp Pro Glu Val
            340                 345                 350
Lys Phe Asn Trp Tyr Val Asp Gly Val Glu Val His Asn Ala Lys Thr
355                 360                 365
Lys Pro Arg Glu Glu Gln Tyr Asn Ser Thr Tyr Arg Val Val Ser Val
        370                 375                 380
Leu Thr Val Leu His Gln Asp Trp Leu Asn Gly Lys Glu Tyr Lys Cys
385                 390                 395                 400
Lys Val Ser Asn Lys Ala Leu Pro Ala Pro Ile Glu Lys Thr Ile Ser
                405                 410                 415
Lys Ala Lys Gly Gln Pro Arg Glu Pro Gln Val Tyr Thr Leu Pro Pro
            420                 425                 430
Ser Arg Asp Glu Leu Thr Lys Asn Gln Val Ser Leu Thr Cys Leu Val
        435                 440                 445
Lys Gly Phe Tyr Pro Ser Asp Ile Ala Val Glu Trp Glu Ser Asn Gly
    450                 455                 460
Gln Pro Glu Asn Asn Tyr Lys Ala Thr Pro Pro Val Leu Asp Ser Asp
465                 470                 475                 480
Gly Ser Phe Phe Leu Tyr Ser Lys Leu Thr Val Asp Lys Ser Arg Trp
                485                 490                 495
Gln Gln Gly Asn Val Phe Ser Cys Ser Val Met His Glu Ala Leu His
            500                 505                 510
Asn His Tyr Thr Gln Lys Ser Leu Ser Leu Ser Pro Gly Lys
        515                 520                 525

<210> SEQ ID NO 21
<211> LENGTH: 954
<212> TYPE: DNA
<213> ORGANISM: artificial sequence
<220> FEATURE:
<223> OTHER INFORMATION: synthetic fragment 1

<400> SEQUENCE: 21
gccaccatgg tcagctactg ggacaccggg gtcctgctgt gcgcgctgct cagctgtctg    60
cttctcacag gatctagttc cggaggtaga cctttcgtag atgtacagtg aaatcccc     120
gaaattatac acatgactga aggaagggag ctcgtcattc cctgccgggt tacgtcacct   180
aacatcactg ttactttaaa aaagttccca cttgacactt tgatccctga tggaaaacgc   240
ataatctggg acagtagaaa gggcttcatc atatcaaatg caacgtacaa agaaataggg   300
cttctgacct gtgaagcaac agtcaatggg catttgtata agacaaacta tctcacacat   360
cgacaaacca atacaatcat agatgtggtt ctgagtccgt ctcatggaat tgaactatct   420
gttggagaaa agcttgtctt aaattgtaca gcaagaactg aactaaatgt ggggattgac   480
ttcaactggg aatacccttc ttcgaagcat cagcataaga aacttgtaaa ccgagaccta   540
aaaacccagt ctgggagtga gatgaagaaa ttttttgagca ccttaactat agatggtgta   600
acccggagtg accaaggatt gtacacctgt gcagcatcca gtgggctgat gaccaagaag   660
aacagcacat ttgtcagggt ccatgaaaaa ccttttgttg cttttggaag tggcatggaa   720
tctctggtgg aagccacggt gggggagcgt gtcagaatcc ctgcgaagta ccttggttac   780
ccacccccag aaataaaatg gtataaaaat ggaatacccc ttgagtccaa tcacacaatt   840
aaagcgggc atgtactgac gattatggaa gtgagtgaaa gagacacagg aaattacact   900
gtcatcctta ccaatcccat ttcaaaggag aagcagagcc atgtggtctc tctg          954
```

<210> SEQ ID NO 22
<211> LENGTH: 708
<212> TYPE: DNA
<213> ORGANISM: artificial sequence
<220> FEATURE:
<223> OTHER INFORMATION: synthetic fragment 2

<400> SEQUENCE: 22

| | | | | | |
|---|---|---|---|---|---|
| gtgtatgtcc | caccgggccc | gggcgacaaa | actcacacat | gcccaccgtg | cccagcacct | 60 |
| gaactcctgg | ggggaccgtc | agtcttcctc | ttccccccaa | aacccaagga | caccctcatg | 120 |
| atctcccgga | cccctgaggt | cacatgcgtg | gtggtggacg | tgagccacga | agaccctgag | 180 |
| gtcaagttca | actggtacgt | ggacggcgtg | gaggtgcata | atgccaagac | aaagccgcgg | 240 |
| gaggagcagt | acaacagcac | gtaccgtgtg | gtcagcgtcc | tcaccgtcct | gcaccaggac | 300 |
| tggctgaatg | gcaaggagta | caagtgcaag | gtctccaaca | aagcccctcc | agcccccatc | 360 |
| gagaaaacca | tctccaaagc | caaagggcag | ccccgagaac | cacaggtgta | caccctgccc | 420 |
| ccatcccggg | atgagctgac | caagaaccag | gtcagcctga | cctgcctggt | caaaggcttc | 480 |
| tatcccagcg | acatcgccgt | ggagtgggag | agcaatgggc | agccggagaa | caactacaag | 540 |
| accacgcctc | ccgtgctgga | ctccgacggc | tccttcttcc | tctatagcaa | gctcaccgtg | 600 |
| gacaagagca | ggtggcagca | ggggaacgtc | ttctcatgct | ccgtgatgca | tgaggctctg | 660 |
| cacaaccact | acacgcagaa | gagcctctcc | ctgtctccgg | gtaaatga | | 708 |

<210> SEQ ID NO 23
<211> LENGTH: 29
<212> TYPE: DNA
<213> ORGANISM: artificial sequence
<220> FEATURE:
<223> OTHER INFORMATION: full length upstream primer , P1

<400> SEQUENCE: 23
atacctaggg ccaccatggt cagctactg                                         29

<210> SEQ ID NO 24
<211> LENGTH: 31
<212> TYPE: DNA
<213> ORGANISM: artificial sequence
<220> FEATURE:
<223> OTHER INFORMATION: full length downstream primer, P2

<400> SEQUENCE: 24
actgtatact catttacccg gagacaggga g                                      31

<210> SEQ ID NO 25
<211> LENGTH: 48
<212> TYPE: DNA
<213> ORGANISM: artificial sequence
<220> FEATURE:
<223> OTHER INFORMATION: non-mutant upstream primer, P3

<400> SEQUENCE: 25
cagagccatg tggtctctct ggttgtgtat gtcccaccgg gcccgggc                    48

<210> SEQ ID NO 26
<211> LENGTH: 49
<212> TYPE: DNA
<213> ORGANISM: artificial sequence
<220> FEATURE:
<223> OTHER INFORMATION: non-mutant downstream primer, P4

<400> SEQUENCE: 26

```
gcccgggccc ggtgggacat acacaaccag agagaccaca tggctctgc         49
```

<210> SEQ ID NO 27
<211> LENGTH: 48
<212> TYPE: DNA
<213> ORGANISM: artificial sequence
<220> FEATURE:
<223> OTHER INFORMATION: upstream primer for producing SEQ ID NO: 2, P5

<400> SEQUENCE: 27

```
cagagccatg tggtctctct gcgtgtgtat gtcccaccgg gcccgggc          48
```

<210> SEQ ID NO 28
<211> LENGTH: 49
<212> TYPE: DNA
<213> ORGANISM: artificial sequence
<220> FEATURE:
<223> OTHER INFORMATION: downstream primer for producing SEQ ID NO: 2,
      P6

<400> SEQUENCE: 28

```
gcccgggccc ggtgggacat acacacgcag agagaccaca tggctctgc         49
```

<210> SEQ ID NO 29
<211> LENGTH: 48
<212> TYPE: DNA
<213> ORGANISM: artificial sequence
<220> FEATURE:
<223> OTHER INFORMATION: upstream primer for producing SEQ ID NO: 4, P7

<400> SEQUENCE: 29

```
cagagccatg tggtctctct gcctgtgtat gtcccaccgg gcccgggc          48
```

<210> SEQ ID NO 30
<211> LENGTH: 48
<212> TYPE: DNA
<213> ORGANISM: artificial sequence
<220> FEATURE:
<223> OTHER INFORMATION: downstream primer for producing SEQ ID NO: 4,
      P8

<400> SEQUENCE: 30

```
gcccgggccc ggtgggacat acacaggcag agagaccaca tggctctg          48
```

<210> SEQ ID NO 31
<211> LENGTH: 48
<212> TYPE: DNA
<213> ORGANISM: artificial sequence
<220> FEATURE:
<223> OTHER INFORMATION: upstream primer for producing SEQ ID NO: 6, P9

<400> SEQUENCE: 31

```
cagagccatg tggtctctcg tcctgtgtat gtcccaccgg gcccgggc          48
```

<210> SEQ ID NO 32
<211> LENGTH: 46
<212> TYPE: DNA
<213> ORGANISM: artificial sequence
<220> FEATURE:
<223> OTHER INFORMATION: downstream primer for producing SEQ ID NO: 6,
      P10

<400> SEQUENCE: 32

```
gcccgggccc ggtgggacat acacaggacg agagaccaca tggctc            46
```